United States Patent
Miwa et al.

(10) Patent No.: US 11,382,978 B2
(45) Date of Patent: *Jul. 12, 2022

(54) PERCUTANEOUS ABSORPTION COMPOSITION

(71) Applicant: MEDRx CO., LTD, Higashikagawa (JP)

(72) Inventors: Yasushi Miwa, Higashikagawa (JP); Hidetoshi Hamamoto, Higashikagawa (JP); Naoya Akazawa, Higashikagawa (JP)

(73) Assignee: MEDRX CO., LTD, Kagawa (JP)

( * ) Notice: Subject to any disclaimer, the term of this patent is extended or adjusted under 35 U.S.C. 154(b) by 7 days.

This patent is subject to a terminal disclaimer.

(21) Appl. No.: 16/782,988

(22) Filed: Feb. 5, 2020

(65) Prior Publication Data

US 2020/0171156 A1 Jun. 4, 2020

Related U.S. Application Data

(63) Continuation of application No. 15/960,392, filed on Apr. 23, 2018, now Pat. No. 10,588,973, which is a continuation of application No. 15/279,210, filed on Sep. 28, 2016, now Pat. No. 9,974,858, which is a continuation of application No. PCT/JP2016/075203, filed on Aug. 29, 2016, which is a continuation-in-part of application No. PCT/JP2015/074553, filed on Aug. 29, 2015.

(51) Int. Cl.
| | |
|---|---|
| *A61K 47/12* | (2006.01) |
| *A61K 31/433* | (2006.01) |
| *A61K 9/00* | (2006.01) |
| *A61K 31/485* | (2006.01) |
| *A61K 9/70* | (2006.01) |

(52) U.S. Cl.
CPC ............ *A61K 47/12* (2013.01); *A61K 9/0014* (2013.01); *A61K 9/7053* (2013.01); *A61K 31/433* (2013.01); *A61K 31/485* (2013.01)

(58) Field of Classification Search
CPC ..... A61K 9/0014; A61K 31/433; A61K 47/12
See application file for complete search history.

(56) References Cited

U.S. PATENT DOCUMENTS

| | | | |
|---|---|---|---|
| 9,974,858 | B2 | 5/2018 | Miwa et al. |
| 2004/0142024 | A1 | 7/2004 | Chono et al. |
| 2009/0130189 | A1 | 5/2009 | Nicklasson et al. |
| 2010/0256174 | A1 | 10/2010 | Yamaguchi et al. |
| 2011/0027365 | A1 | 2/2011 | Chono et al. |
| 2011/0028880 | A1 | 2/2011 | Uchida et al. |
| 2011/0152377 | A1 | 6/2011 | Hanma et al. |
| 2012/0226245 | A1 | 9/2012 | Kawamura et al. |
| 2013/0165522 | A1 | 6/2013 | Scheppler et al. |
| 2014/0066471 | A1 | 3/2014 | Yamaguchi et al. |

FOREIGN PATENT DOCUMENTS

| | | |
|---|---|---|
| CN | 101143127 A | 3/2008 |
| JP | 61-172830 | 8/1986 |
| JP | 2007-008871 A | 1/2007 |
| JP | 2009-529011 A | 8/2009 |
| JP | 2012-158521 A | 8/2012 |
| JP | 2013-528632 | 7/2013 |
| JP | 2014-125483 A | 7/2014 |
| KZ | 6622 | 10/1998 |
| RU | 2334507 | 4/2008 |
| WO | WO 2001/07018 | 2/2001 |
| WO | WO 2009/066457 | 5/2009 |
| WO | WO 2009/107479 | 9/2009 |
| WO | WO 2010/016219 | 2/2010 |
| WO | WO 2011/027786 | 3/2011 |
| WO | WO 2011/157449 | 12/2011 |

OTHER PUBLICATIONS

T. Mundorf et al. "A 12-Month, Multicenter, Randomized, Double-Masked, Parallel-Group Comparison of Timolol-LA Once Daily and Timolol Maleate Opthalmic Solution Twice Daily in the Treatment of Adults with Glaucoma or Ocular Hypertension", pp. 541-551, 2004, in 6 pages.

Extended European Search Report, Application No. PCT/JP2016/075203, dated Jun. 26, 2018, in 8 pages.

PCT International Search Report, Application No. PCT/JP2016/075203, dated Oct. 3, 2016, in 2 pages.

PCT International Preliminary Report on Patentability, Application No. PCT/JP2016/075203, dated Aug. 29, 2016, in 8 pages.

Mutalik S, Parekh HS, Davies NM, Udupa N. A combined approach of chemical enhancers and sonophoresis for the transdermal delivery of tizanidine hydrochloride. Drug Deliv. Feb. 2009; 16(2):82-91. PMID: 19267299 (Year: 2009).

*Primary Examiner* — Theodore R. Howell
(74) *Attorney, Agent, or Firm* — Morgan, Lewis & Bockius LLP

(57) ABSTRACT

The embodiments provide a percutaneous absorption composition for a basic medicament having improved transdermal absorbability. The percutaneous absorption composition comprises a sorbic acid and/or a metal sorbate as a percutaneous absorption promotor. The molar ration of the sorbic acid and/or the metal sorbate to the basic medicament is 0.5-2.5. The composition of the present disclosure may further comprise a basic component.

20 Claims, No Drawings

PERCUTANEOUS ABSORPTION COMPOSITION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to an external preparation containing a basic medicament. Specifically, the present invention relates to a composition containing sorbic acid as a transdermal absorption accelerator.

Description of the Related Art

Several techniques for improving percutaneous absorption of a basic medicament are known. For example, the lipid solubility of a basic medicament may be adjusted by forming an equimolar salt of the basic medicament and an organic acid (Patent Document 1). An ionic liquid consisting of an aliphatic acid and an organic amine compound has also been used as a transdermal absorption accelerator (Patent Document 2). However for some medicaments, better absorbability was still required or a long-term stable formulation couldn't be obtained with conventional technique.

Sorbic acid is known as an antiseptic gent, and can be utilized for a water-based adhesive patch such as cataplasms (Patent Document 3). However, it has not been known that sorbic acid can exhibit an excellent transdermal absorbability accelerating effect for the basic medicament. Neither using them as a transdermal absorption accelerator nor a non-aqueous absorption composition has been known.

PRIOR ART DOCUMENTS

Patent Documents

Patent Document 1: WO2010/016219
Patent Document 2: WO2009/066457
Patent Document 3: JP2014-125483A

SUMMARY OF THE INVENTION

Problem to be Solved

An object of the present invention is to provide a percutaneous absorption composition which exhibits an excellent percutaneous absorbability of a basic medicament and a percutaneous absorption promoter for the basic medicament.

As a result of intensive investigation, the present inventors has found that sorbic acid exhibits an excellent accelerating effect for percutaneous absorption of basic medicament, and the effect can be further increased by using sorbic acid in combination with a basic component.

The present invention provides the following (1) to (5);
(1) A percutaneous absorption composition comprising a basic medicament or a salt thereof and sorbic acid and/or its metal salt.
(2) The percutaneous absorption composition described in above (1), wherein a concentration of the sorbate component is 0.5-2.5 mol with respect to 1 mol of the basic medicament.
(3) The percutaneous absorption composition described in above (1) or (2), further comprising an organic basic compound and/or an inorganic basic component.
(4) The percutaneous absorption composition described in above (3), wherein the concentration of the organic basic compound and/or inorganic basic component is 0.4-3.0 mol with respect to 1 mol of the sorbate component.
(5) A percutaneous absorption promoter for a basic medicament comprising sorbic acid and/or its metal salt, and an organic basic compound and or an inorganic basic component.

Effect of the Invention

According to the present invention, a percutaneous absorption composition which exhibits an excellent transdermal permeability of basic medicament and a percutaneous absorption promoter for basic medicament with excellent transdermal absorption accelerating effect are provided.

DETAILED DESCRIPTION OF THE PREFERRED EMBODIMENT

Certain embodiments provide a percutaneous absorption composition comprising an basic medicament or a salt thereof, and a sorbate component. The sorbate component may include a sorbic acid and/or metal sorbate. In some embodiments, the percutaneous absorption promoter for a basic medicament of the present disclosure comprises a sorbate component. In some embodiments, the percutaneous absorption promoter may further comprise a basic component.

Basic Medicament

In some embodiments, a basic medicament has a basic functional group, such as an amino group. Specifically, a hypnotic/sedative agent such as flurazepam, rilmazafone, medetomidine, dexmedetomidine; a stimulant/antihypnotic agent such as methamphetamine, methylphenidate; a psychoneurotic agent such as imipramine, diazepam, sertraline, fluvoxamine, paroxetine, citalopram, fluoxetine, alprazolam, haloperidol, clomipramine, amitriptyline, desipramine, amoxapine, maprotiline, mirtazapine, setiptiline, duloxetine, diazepam, etizolam; a topical anesthesia such as lidocaine, procaine, tetracaine, dibucaine; an agent for urinary such as oxybutynin, tamsulosin, propiverine, imidafenacin, solifenacin, darifenacin, tolterodine, an muscle relaxant suxamethonium such as tizanidine, eperisone, pridinol, suxamethonium; an agent for genital organs such as ritodrine, meluadrine; an antiparkinsonian agent such as pergolide, bromocriptine, trihexyphenidyl, amantadine, ropinirole, talipexole, pramipexole, rotigotine, cabergoline, Selegiline, rasagiline; an anti-migraine agent such as dihydroergotamine, sumatriptan, ergotamine, flunarizine, cyproheptadine; an antihistamine agent such as clemastine, diphenhydramine, chlorpheniramine, diphenylpyraline; a bronchodilator agent such as tulobuterol, procaterol, salbutamol, clenbuterol, fenoterol, terbutaline, isoprenaline, a cardiotonic agent such as denopamine, a peripheral vasodilators such as nicametate, tolazoline; a smoking-cessation aid such as nicotine, varenicline; a cardiovascular preparation such as atenolol, bisoprolol, metoprolol, carvedilol, carteolol, valsartan, clonidine; an antiarrhythmic agent such as propranolol, alprenolol, procainamide, mexiletine; prophylactic agent for digestive ulcer such as proglumide, cetraxate, spizofurone, cimetidine; a gastrointestinal motility improving agent such as domperidone, cisapride; an anti-allergy agent such as ketotifen, azelastine, emedastine; an antiviral agent such as acyclovir; an alzheimer's disease treating e agent such as donepezil, tacrine, arecoline, galantamine, rivastigmine; an serotonin receptor antagonist/antiemetic agent such as ondansetron, granisetron, ramosetron, azasetron; an opioid analgesic such as morphine, codeine, fentanyl, oxycodone, hydromorphone; an antifungal agent such as terbinafine, butenafine, amorolfine, neticonazole, miconazole, luliconazole, itraconazole can be exemplified.

The basic medicament is preferably used in a state of its pharmaceutically acceptable acid addition salt due to its stability and low dermal irritancy, though it can also be utilized in its free state. Examples of the acid addition salt include an inorganic salt such as hydrochloride salt, sulfate salt, and hydrobromate; and an organic salt such as fumarate, maleate, citrate, and tartrate.

The basic medicament can be used alone or in combination with one or more other basic medicament. In some embodiments, the basic medicament may be selected from the group consisting of tizanidine hydrochloride, oxycodone hydrochloride, lidocaine hydrochloride, and a combination thereof. In some embodiments, the basic medicament may comprise at least one compound selected from tizanidine hydrochloride, and oxycodone hydrochloride.

Sorbate Component

Sorbic acid accelerates percutaneous absorption of basic medicament. Without being bound to the theory, sorbic acid may bind ionically to the basic medicament to form an ionic liquid in the composition. In some embodiments, the ionic liquid may be tizanidine sorbate, oxycodone sorbate or lidocaine sorbate. Both the free sorbic acid and a metal salt of sorbic acid such as sodium sorbate, potassium sorbate, and calcium sorbate, can be used. In some embodiments, the free sorbic acid and a metal salt of sorbic acid can also be used in combination. When the sorbic acid and metal salt of sorbic acid are used in combination, the term "sorbate component" also refers to sorbic acid and metal salt of sorbic acid collectively. In this case, the term "concentration of sorbate component" as used in this application denotes total amount of the sorbic acid and the metal salt of sorbic acid together. In cases where either sorbic acid or metal salt of sorbic acid is used alone, the term "concentration of sorbate component" denotes the amount of the sorbic acid or the metal salt of sorbic acid.

The concentration of sorbate component can be selected from the range of, for example about 0.1 to about 3.0 mol, about 0.5 to about 2.5 mol, and about 0.9 to about 2.1 mol per 1 mol of the basic medicament. In some embodiments, the percutaneous absorption accelerating effect is remarkable when the concentration of the sorbate component is between about 0.5 mol and about 2.5 mol. However, the concentration of over 3 mol may sometimes reduce the permeability of medicament.

Basic Component

In some embodiments, the composition of the present disclosure may further comprise a basic component. The basic component may include one or more of organic basic compound, inorganic basic compound, and salt of a strong base. By using the basic component in combination with above-mentioned sorbate component, percutaneous absorbability of the basic medicament can be further improved. Thus, the combination of the basic component and the sorbate component can thus be utilized as an excellent transdermal absorption accelerator.

In some embodiments, the organic basic compound may be a $C_{2-9}$ alkanolamine such as monoethanolamine, monoisopropanolamine, diethanolamine, diisopropanolamine, triethanolamine, triisopropanolamine, ethylenediamine, and trishydroxymethylaminomethane (trometamol), or a basic amino acid such as arginine. In some embodiments, the organic basic compound is an organic amine compound having three hydroxyl groups in a molecule, such as triethanolamine, triisopropanolamine, or trishydroxymethylaminomethane. In some embodiments, the organic basic compound is triethanolamine. The composition may comprise one or more organic basic compounds.

In some embodiments, the inorganic basic compound is a compound containing an alkali metal or an alkali earth metal. Examples of inorganic basic compound include hydroxide such as sodium hydroxide, potassium hydroxide, calcium hydroxide. In some embodiments, the salt of a strong base includes a metal salt of carboxylic acid such as sodium benzoate, sodium propionate, calcium propionate, sodium fumarate, sodium sorbate, and potassium sorbate; a metal salt of hydroxyl acid such as sodium lactate, sodium tartrate, potassium tartrate, and sodium citrate; sodium sulfite; and sodium pyrosulfite. In some embodiments, when the metal salt of sorbic acid, such as potassium sorbate, is used as the "sorbate component," it may be classified not only as a "sorbate component," but also as a "basic component". Thus, when calculating the amount for each component, the amount of metal salt of sorbic acid should be counted both as a part of the "sorbate component" and a part of the "basic component".

In some embodiments, when a hydrochloride of a basic medicament is present as an active ingredient, and a basic component is also present in the composition, the metallic ions which constitutes the inorganic basic compound and/or the salt of a strong base can behave as a "hydrochloric acid scavenger" as well. The metallic ion scavenges hydrochloric acid attached to the basic medicament to form hydrochloride, thus generates the free form of the basic medicament and improves the skin permeability of the medicament.

The amount of the basic component can be within the range of about 0.4 mol to about 3.0 mol, about 0.5 mol to about 2.5 mol, about 0.5 mol to about 2.0 mol, or about 0.5 mol to about 1.6 mol per 1 mol of sorbate component.

Other Percutaneous Absorption Accelerator

In some embodiments, the composition of the present disclosure may further include one or more compound that can dissolve the medicament and sorbic acid, and having percutaneous absorption accelerating effect on the medicament. For examples, percutaneous absorption accelerator such as aliphatic acid, alcohol, ester compound, and amide compound may be useful. The composition of the present invention is a non-aqueous composition which does not substantially contain water. For example, the non-aqueous composition contains less than about 3.0%, or less than about 1.0% water.

As used herein, the aliphatic acid as a percutaneous absorption accelerator may include one or more $C_{4-20}$ saturated or unsaturated aliphatic acid, excluding sorbic acid. Examples of the aliphatic acid include levulinic acid, capric acid, lauric acid, myristic acid, palmitic acid, stearic acid, isostearic acid, and oleic acid. In some embodiments, the composition further contains at least one unsaturated aliphatic acid. In some embodiments, the unsaturated aliphatic acid is oleic acid. When the aliphatic acid is present in the composition, the total concentration of sorbate component and the aliphatic acid is about 0.8 mol to about 2.5 mol, or about 0.8 mol to about 2.0 mol per 1 mol of the basic component. In some embodiment, the total weight of the sorbate component and the aliphatic acid may be about 2.0% to about 3.0% by weight, or about 2.0% to about 2.5% by weight of the total weight of the adhesive layer.

In some embodiments, the composition may further contain an alcohol. The alcohol may be monovalent alcohol such as lauryl alcohol, myristyl alcohol, oleyl alcohol, isostearyl alcohol, and cetyl alcohol; divalent alcohol such as propylene glycol, butylene glycol, dipropylene glycol, diisobutylene glycol, polyethylene glycol, and hexylene glycol; or trivalent alcohol such as glycerin, and hexanetriol. In some embodiments, the composition may include two or more alcohols. In some embodiments, the composition contains oleyl alcohol.

In some embodiments, the composition may also contain an ester compound. The ester compound may be diethyl sebacate, methyl laurate, diisopropyl adipate, isopropyl myristate, or medium-chain triglyceride. Medium-chain triglyceride may include triglycerides whose fatty acids have $C_{6-12}$ aliphatic chain. In some embodiments, the composition may further contain an amide compound, such as lauric acid diethanolamide.

In some embodiments, the composition can be provided as a homogeneous solution prepared by mixing the basic medicament and/or salt thereof, sorbate component, and the basic component with a solvent. In some embodiments, the composition further comprises an aliphatic acid, an alcohol, and/or an ester compound.

Matrix Type Plaster

A matrix type plaster can be obtained from the composition of the present composition by dispersing above mentioned solution in an adhesive layer comprising an appropriate polymer. The useful polymer may include acrylic polymer, rubber polymer, silicone polymer, or vinyl ether-based polymer. In some embodiments, a rubber polymer such as styrene-isoprene-styrene block copolymer, styrene-butadiene-styrene block copolymer, polyisoprene, polyisobutylene, and/or polybutadiene can be utilized. The concentration of the rubber polymer may be about 5% to about 40% by weight, or about 10% to about 30% by weight, or about 5% to about 25% of the total weight of the dried adhesive layer. The concentration of the acrylic polymer or silicone polymer may be about 45% to about 95% by weight, or about 50% to about 90% by weight of the total weight of the dried adhesive layer.

In some embodiments, the adhesive layer further contains a filler. The filler can improve not only the adhesion of the adhesive layer, but also the drug release rate. The concentration of the filler can be about 0.5% to about 5% by weight of the total weight of the adhesive layer. The filler may be selected from hydrous silica, fumed silica, talc, crystalline cellulose, starch, carmellose, and metal salt of carmellose. In some embodiments, the filler may be the fumed silica. A commercially available fumed silica, AEROSIL®, is an example.

The adhesive layer may further contain other additives such as tackifier resin, softener, and/or antioxidant. Examples of a tackifier resin include rosin ester, hydrogenated rosin ester, rosin maleate, alicyclic saturated hydrocarbon resin, terpene resin, and polyolefin resin. Examples of the softener include naphthenic processing oil; vegetable oil such as camellia oil, castor oil; liquid rubber such as liquid polybutene, liquid isoprene robber; and liquid paraffin. Examples of the antioxidant include butyl hydroxyl toluene, ascorbic acid, propyl gallate, sodium sulfite, and sodium pyrosulfite.

When the matrix type plaster is prepared from the composition disclosed herein, the concentration of the basic medicament can be about 0.5% to about 10% by weight, or about 1% to about 5% by weight of the total amount of the dried adhesive layer. Additionally, in some embodiments, at least two of monovalent alcohol such as oleyl alcohol, divalent alcohol such as butylene glycol, propylene glycol, and trivalent alcohol such as glycerin are used in combination. In some embodiments, the concentration of the alcohols can be about 15% to about 35% by weight, about 20% to about 30% by weight, or about 22% to about 28% by weight of the dried adhesive layer.

EXAMPLES

Hereinafter, the present disclosure is explained in detail with examples. The present disclosure is not limited in any way by these examples.

Example 1: Preparing an Adhesive Patch Containing Tizanidine and Sorbic Acid

Tizanidine hydrochloride, sorbic acid, sodium lactate, sodium benzoate, triethanolamine, diethyl sebacate, isopropyl myristate, glycerin, DiPG(dipropylene glycol), oleyl alcohol, propyl gallate, and liquid paraffin are mixed, then heated (60° C.) and dissolved to yield a homogeneous solution. Terpene resin dissolved in toluene, styrene-isoprene-styrene block copolymer (SIS5002) dissolved in toluene, and fumed silica were added to the solution and uniformly mixed to yield an adhesive composition containing the active ingredient. The obtained adhesive composition containing the active ingredient are coated onto the PET film. Then, it was dried for 10 minutes at 80° C. to eliminate toluene. Thus adhesive patch containing tizanidine and sorbic acid was prepared. Amount (weight %) of each component is as shown in table 1.

Comparative Example 1: Preparing an Adhesive Patch Containing Tizanidine

Adhesive patches containing the composition (weight %) shown in Table 1 was prepared by using the similar procedure as described in Example 1.

Example 2 and Comparative Example 2: Preparing Adhesive Patches Containing Oxycodone Adhesive patches containing oxycodone as the composition (weight %) shown in Table 1 was prepared by using the similar procedure as described in Example 1.

In Vitro Transdermal Permeation Study

Transdermal permeation of medicament was evaluated with the use of Franz cell for each adhesive patches prepared in Examples and Comparative Examples. Cumulative skin permeation amount at each sampling points are shown in Table 1. Hairless rat abdominal skin was used for the adhesive patches containing tizanidine prepared in Example 1 and Comparative Example 1, pig skin was used for the adhesive patches containing oxycodone prepared in Example 2 and Comparative Example 2.

TABLE 1

| | | Ex. 1-1 Q907 | Com. 1-1 Q914 | Com. 1-2 Q910 | Com. 1-3 Q137 | Com. 1-4 Q891 | Ex. 2-1 M304 | Ex. 2-2 M305 | Com. 2-1 M300 | Com. 2-2 M292 |
|---|---|---|---|---|---|---|---|---|---|---|
| Tizanidine Hydrochloride | | 1.72 | 1.72 | 1.72 | 1.72 | 1.72 | | | | |
| Oxycodone Hydrochloride | | | | | | | 3.461 | 3.461 | 3.461 | 3.461 |
| Sorbic Acid | | 1.33 | | | | | 0.70 | 1.30 | | |
| Potassium sorbate | | | | | | | 1.30 | | | |
| Levulinic acid | | | 0.69 | 1.38 | | | | | 1.00 | |
| Isostearic acid | | | | | | 3.00 | | | | |
| Oleic acid | | | | | 4.00 | 1.00 | 3.00 | 3.00 | 4.00 | 4.00 |
| Sodium lactate | | 0.73 | 0.73 | 0.73 | 0.73 | 0.73 | | | | |
| Sodium benzoate | | 0.2 | 0.2 | 0.2 | 0.2 | 0.2 | | | | |
| Potassium hydroxide | | | | | | | | | 0.55 | |
| Triethanolamine | | 2.00 | 1.00 | 0.50 | 0.50 | 0.50 | | | | |
| Diisopropanolamine | | | | | | | 1.50 | 1.50 | 1.50 | 1.50 |
| Diethyl sebacate | | 5.00 | 5.00 | 5.00 | 5.00 | 5.00 | | | | |
| Isopropyl myristate | | 5.00 | 5.00 | 5.00 | 5.00 | 5.00 | | | | |
| Medium-chain triglyceride | | | | | | | 10.00 | 10.00 | 10.00 | 10.00 |
| Propylene carbonate | | | | | | | 5.00 | 5.00 | 5.00 | 3.00 |
| Glycerin | | 5.00 | 5.00 | 5.00 | 10.00 | 5.00 | 4.00 | 4.00 | 3.00 | 5.00 |
| propylene glycol | | 4.00 | 4.00 | 4.00 | | | | | | |
| Butylene glycol | | 3.00 | 3.00 | 3.00 | | | | | | |
| Oleyl alcohol | | 10.00 | 10.00 | 10.00 | 10.00 | 10.00 | 10.00 | 10.00 | 10.00 | 3.00 |
| PEG200 | | | | | | | | | | 7.00 |
| Benzyl alcohol | | | | | | 4.00 | | | | |
| Sodium pyrosulfite | | 0.10 | 0.10 | 0.10 | 0.10 | 0.10 | 0.10 | 0.10 | 0.10 | 0.10 |
| Propyl gallate | | 0.05 | 0.05 | 0.05 | 0.05 | 0.05 | 0.05 | 0.05 | 0.05 | 0.05 |
| AEROSIL ® | | 3 | 3 | 3 | 3 | 3 | 3 | 3 | 3 | 3 |
| Liquid paraffin | | 10.87 | 12.51 | 12.32 | 11.7 | 12.7 | 16.91 | 17.61 | 17.34 | 17.89 |
| Terpene resin | | 32 | 32 | 32 | 32 | 32 | 26 | 26 | 26 | 27 |
| SIS5002 | | 16 | 16 | 16 | 16 | 16 | 15 | 15 | 15 | 15 |
| Total | | 100 | 100 | 100 | 100 | 100 | 100 | 100.02 | 100 | 100 |
| (base)/(sorbic acid) | | 1.84 | | | | | 1.37 | 1.02 | | |
| (sorbic acid)/(API) | | 2.00 | | | | | 1.75 | 1.36 | | |
| (aliphatic acid)/(base) | | 0.54 | 0.39 | 1.01 | 1.20 | 1.20 | 1.25 | 1.88 | 1.05 | 1.20 |
| Cumulative skin | 2 hr | 21.3 | 6.5 | 1.8 | 3.6 | 3.8 | 0.881 | 0.675 | | 0.235 |
| permeation | 4 hr | 80.7 | 28.2 | 10.4 | 11.9 | 15.5 | 10.39 | 11.23 | 0.491 | 8.577 |
| amount | 6 hr | 135.3 | 49.8 | 24.9 | 24.4 | 30.6 | | | | |
| ($\mu$g/cm$^2$) | 8 hr | 172.3 | 71.5 | 40.1 | 39.8 | 46.7 | 36.12 | 73.08 | 4.059 | 44.9 |
| | 10 hr | 192.8 | 87.9 | 55.8 | 56.9 | 62.4 | | | | |
| | 24 hr | | | | | | 348.5 | 318.2 | 40.22 | 197.2 |

The adhesive patch of Example 1-1 containing sorbic acid exhibited higher transdermal permeability relative to that of Comparative Example 1-1 to 1-4 containing higher fatty acid instead of sorbic acid. Adhesive patches of Example 2 and Comparable Example 2 containing oxycodone instead of tizanidine also showed similar results as those containing tizanidine. That is, adhesive patches of present invention containing sorbic acid (Examples 2-1 and 2-2) exhibited higher skin permeability relative to adhesive patches Example 3: Investigation of the Optimum Amount of Sorbic Acid and Basic Component Adhesive patches as the composition (weight %) shown in Table 2 were prepared. In vitro transdermal permeability test with use of rat skin was conducted for the obtained patches. The results are shown in Table 2.

TABLE 2

| | Ex. 3-1 Q909 | Ex. 3-2 Q907 | Ex. 3-3 Q906 | Ex. 3-4 Q900 | Ex. 3-5 Q899 | Ex. 3-6 Q898 | Ex. 3-7 Q901 | Ex. 3-8 Q897 | Ex. 3-9 Q905 |
|---|---|---|---|---|---|---|---|---|---|
| Tizanidine Hydrochloride | 1.72 | 1.72 | 1.72 | 1.72 | 1.72 | 1.72 | 1.72 | 1.72 | 1.72 |
| Sorbic Acid | 0.66 | 0.33 | 0.33 | 0.33 | 0.33 | 0.33 | 2.65 | 2.65 | 3.32 |
| Sodium lactate | 0.73 | 0.73 | 0.73 | 0.73 | 0.73 | 0.73 | 0.73 | 0.73 | 0.73 |
| Sodium benzoate | 0.20 | 0.20 | 0.20 | 0.20 | 0.20 | 0.20 | 0.20 | 0.20 | 0.20 |
| Triethanolamine | 1.50 | 2.00 | 1.50 | 1.00 | 0.50 | 0.00 | 1.00 | 0.50 | 0.00 |
| Diethyl sebacate | 5.00 | 5.00 | 5.00 | 5.00 | 5.00 | 5.00 | 5.00 | 5.00 | 5.00 |
| Isopropyl myristate | 5.00 | 5.00 | 5.00 | 5.00 | 5.00 | 5.00 | 5.00 | 5.00 | 5.00 |
| Glycerin | 5.00 | 5.00 | 5.00 | 5.00 | 5.00 | 5.00 | 5.00 | 5.00 | 5.00 |
| propylene glycol | 4.00 | 4.00 | 4.00 | 4.00 | 4.00 | 4.00 | 4.00 | 4.00 | 4.00 |
| Butylene glycol | 3.00 | 3.00 | 3.00 | 3.00 | 3.00 | 3.00 | 3.00 | 3.00 | 3.00 |
| Oleyl alcohol | 10.00 | 10.00 | 10.00 | 10.00 | 10.00 | 10.00 | 10.00 | 10.00 | 10.00 |
| AEROSIL ® | 3 | 3 | 3 | 3 | 3 | 3 | 3 | 3 | 3 |
| Sodium pyrosulfite | 0.10 | 0.10 | 0.10 | 0.10 | 0.10 | 0.10 | 0.10 | 0.10 | 0.10 |
| Propyl gallate | 0.05 | 0.05 | 0.05 | 0.05 | 0.05 | 0.05 | 0.05 | 0.05 | 0.05 |
| Liquid paraffin | 12.04 | 10.87 | 11.37 | 11.87 | 12.37 | 12.87 | 10.55 | 11.05 | 10.88 |

TABLE 2-continued

|  |  | Ex. 3-1 Q909 | Ex. 3-2 Q907 | Ex. 3-3 Q906 | Ex. 3-4 Q900 | Ex. 3-5 Q899 | Ex. 3-6 Q898 | Ex. 3-7 Q901 | Ex. 3-8 Q897 | Ex. 3-9 Q905 |
|---|---|---|---|---|---|---|---|---|---|---|
| Terpene resin |  | 32.00 | 32.00 | 32.00 | 32.00 | 32.00 | 32.00 | 32.00 | 32.00 | 32.00 |
| SIS5002 |  | 16.00 | 16.00 | 16.00 | 16.00 | 16.00 | 16.00 | 16.00 | 16.00 | 16.00 |
| Total |  | 100 | 100 | 100 | 100 | 100 | 100 | 100 | 100 | 100 |
| (base)/(sorbic acid) |  | 3.05 | 1.08 | 1.51 | 1.23 | 0.95 | 0.67 | 0.62 | 0.48 | 0.27 |
| (sorbic acid)/(API) |  | 0.99 | 2.00 | 2.00 | 2.00 | 2.00 | 2.00 | 3.99 | 3.99 | 5.00 |
| Cumulative skin permeation amount ($\mu g/cm^2$) | 2 hr | 10.08 | 21.30 | 4.40 | 14.70 | 5.80 | 4.7 | 3.40 | 3.10 | 3.50 |
|  | 4 hr | 35.20 | 80.70 | 29.40 | 53.80 | 33.70 | 28.9 | 25.60 | 24.00 | 20.80 |
|  | 6 hr | 54.00 | 135.30 | 63.70 | 91.30 | 66.50 | 57.6 | 48.20 | 47.50 | 45.40 |
|  | 8 hr | 66.70 | 172.30 | 93.00 | 119.30 | 99.40 | 85.7 | 71.90 | 72.50 | 66.90 |
|  | 10 hr | 77.30 | 192.80 | 115.20 | 137.70 | 123.60 | 107.5 | 87.30 | 93.50 | 82.80 |

Adhesive patch of Example 3-1 exhibited slightly less transdermal permeability because the ratio of sorbic acid to basic component is small, though all adhesive patches of Examples from 3-1 to 3-9 containing sorbic acid exhibited excellent skin permeability. Adhesive patches of Example 3-7 to 3-9 contain excessive amounts of sorbic acid relative to tizanidine, and also exhibited slightly less transdermal permeability.

Investigation of Optimum Basic Component

Adhesive patches containing sorbic acid and a variety of basic component as the composition (weight %) shown in Table 3 were prepared. In vitro transdermal permeability test with use of rat skin was conducted for the obtained patches. The results are shown in Table 3.

All adhesive patches of Examples 4-1 to 4-8 exhibited excellent transdermal permeability. It is considered because they contain sorbic acid, and ratio of sorbic acid to the medicament and ratio of basic component to sorbic acid are both appropriate.

Example 5

Adhesive patches containing the composition (weight %) shown in Table 4 were prepared. In vitro transdermal permeability test with use of pig skin was conducted for the obtained patches. The results are shown in Table 4.

TABLE 3

|  | Ex. 4-1 Q916 | Ex. 4-2 Q949 | Ex. 4-3 Q950 | Ex. 4-4 Q162 | Ex. 4-5 Q161 | Ex. 4-6 Q163 | Ex. 4-7 Q899 | Ex. 4-8 Q946 |
|---|---|---|---|---|---|---|---|---|
| Tizanidine Hydrochloride | 1.72 | 1.72 | 1.72 | 1.72 | 1.72 | 1.72 | 1.72 | 1.72 |
| Sorbic Acid | 1.33 | 1.33 | 1.33 | 1.33 | 1.33 | 1.33 | 1.33 | 0.66 |
| Potassium sorbate |  |  |  |  |  |  |  | 0.89 |
| Sodium lactate | 0.73 |  |  |  |  |  | 0.73 |  |
| Sodium benzoate | 0.20 |  |  |  |  |  | 0.20 |  |
| Sodium hydroxide |  |  |  | 0.24 | 0.24 | 0.24 | 0.24 | 0.24 |
| Triethanolamine | 0.50 |  |  | 0.25 | 0.50 | 1.00 | 0.50 | 0.50 |
| Arginine |  |  | 1.03 |  |  |  |  |  |
| Trometamol | 0.72 | 0.72 |  |  |  |  |  |  |
| Diethyl sebacate | 5.00 | 5.00 | 5.00 | 5.00 | 5.00 | 5.00 | 5.00 | 5.00 |
| Isopropyl myristate | 5.00 | 5.00 | 5.00 | 5.00 | 5.00 | 5.00 | 5.00 | 5.00 |
| Glycerin | 5.00 | 5.00 | 5.00 | 5.00 | 5.00 | 5.00 | 5.00 | 5.00 |
| propylene glycol | 4.00 | 4.00 | 4.00 |  |  |  | 4.00 |  |
| Butylene glycol | 3.00 | 3.00 | 3.00 | 4.00 | 4.00 | 4.00 | 3.00 | 4.00 |
| Oleyl alcohol | 10.00 | 10.00 | 10.00 | 10.00 | 10.00 | 10.00 | 10.00 | 10.00 |
| AEROSIL ® | 3.00 | 3.00 | 3.00 | 3.00 | 3.00 | 3.00 | 3.00 | 3.00 |
| Sodium pyrosulfite | 0.10 | 0.20 | 0.20 | 0.10 | 0.20 | 0.10 | 0.10 | 0.10 |
| Propyl gallate | 0.05 | 0.05 | 0.05 | 0.05 | 0.05 | 0.05 | 0.05 | 0.05 |
| Liquid paraffin | 11.65 | 13.08 | 12.77 | 11.31 | 11.06 | 10.56 | 10.37 | 11.08 |
| Terpene resin | 32.00 | 32.00 | 32.00 | 32.00 | 32.00 | 32.00 | 32.00 | 32.00 |
| SIS5002 | 16.00 | 16.00 | 16.00 | 16.00 | 16.00 | 16.00 | 16.00 | 16.00 |
| Total | 100.00 | 100.10 | 100.10 | 95.00 | 95.10 | 95.00 | 98.24 | 95.24 |
| (base)/(sorbic acid) | 1.45 | 0.50 | 0.50 | 0.65 | 0.79 | 1.07 | 1.45 | 1.29 |
| (sorbic acid)/(tizanidine) | 2.00 | 2.00 | 2.00 | 2.00 | 2.00 | 2.00 | 2.00 | 1.99 |
| Cumulative skin permeation amount after 8 hr ($\mu g/cm^2$) | 166.50 | 137.00 | 147.00 | 114.00 | 116.00 | 125.00 | 126.00 | 135.00 |

TABLE 4

|  |  | Ex. 5-1 T651 | Ex. 5-2 T695 | Ex. 5-3 T697 | Ex. 5-4 T700 | Ex. 5-5 T702 | Ex. 5-6 T696 | Ex. 5-7 T739 |
|---|---|---|---|---|---|---|---|---|
| Tizanidine Hydrochloride | | 1.72 | 1.72 | 1.72 | 1.72 | 1.72 | 1.72 | 1.72 |
| Sorbic Acid | | 0.66 | | | | | | |
| Potassium sorbate | | | 0.89 | 0.89 | 0.89 | 0.89 | 0.89 | 0.89 |
| Oleic acid | | | 1.50 | 1.50 | 1.50 | 1.50 | 1.50 | 1.50 |
| Triethanolamine | | 0.5 | 0.5 | 0.4 | | | | |
| Oleyl alcohol | | 10.00 | 10.00 | 10.00 | 10.00 | 10.00 | 10.00 | 10.00 |
| Myristyl alcohol | | | 3.0 | 3.0 | | 3.0 | 3.0 | |
| Glycerin | | 5.00 | 5.00 | 5.00 | 5.00 | 5.00 | 5.00 | |
| Concentrated glycerin | | | | | | | | 5.00 |
| Purified water | | | | | | | | 0.50 |
| Propylene glycol | | 4.00 | 4.00 | 4.00 | 4.00 | 4.00 | 4.00 | 8.00 |
| Butylene glycol | | 3.00 | 3.00 | 3.00 | 3.00 | 3.00 | 3.00 | 3.00 |
| Medium-chain triglyceride | | 5.0 | | | | | | |
| AEROSIL ® | | 3 | 3 | 3 | 3 | 3 | 3 | 3 |
| Liquid paraffin | | 18.08 | 23.24 | 23.34 | 26.74 | 23.74 | 23.74 | 22.24 |
| Terpene resin | | 32.00 | 28.00 | 28.00 | 28.00 | 28.00 | 28.00 | 28 |
| SIS5002 | | 16.00 | 16.00 | 16.00 | 16.00 | 16.00 | 16.00 | 16 |
| Sodium sulfite | | | 0.10 | 0.10 | 0.10 | 0.10 | 0.10 | 0.10 |
| Sodium pyrosulfite | | 0.10 | 0.10 | 0.10 | 0.10 | 0.10 | 0.10 | |
| Propyl gallate | | 0.05 | 0.05 | 0.05 | 0.05 | 0.05 | 0.05 | 0.05 |
| Total | | 100 | 100 | 100 | 100 | 100 | 100 | 100 |
| (base)/(sorbic acid) | | 0.83 | 1.70 | 1.59 | 1.13 | 1.13 | 1.13 | 1.13 |
| (Sorbate component)/(tizanidine) | | 1.99 | 1.00 | 1.00 | 1.00 | 1.00 | 1.00 | 1.00 |
| (aliphatic acid)/(base) | | 1.20 | 1.12 | 1.20 | 1.67 | 1.67 | 1.67 | 1.67 |
| Cumulative skin permeation amount ($\mu g/cm^2$) | 4 hr | 0.4 | 2.1 | 1.9 | 3.6 | 0.8 | 2.4 | 3.5 |
| | 6 hr | 1.6 | 5.8 | 5.7 | 7.0 | 2.7 | 8.5 | 8.1 |
| | 8 hr | 4.5 | 10.5 | 11.0 | 12.0 | 6.1 | 17.7 | 14.6 |
| | 22 hr | 84.0 | 51.2 | 54.5 | 98.7 | 57.8 | 105.2 | 91.9 |
| | 24 hr | 98.5 | 56.1 | 58.9 | 77.3 | 66.4 | 112.5 | 103.3 |

When potassium sorbate was used as sorbate component, excellent transdermal permeability was observed in common with when sorbic acid was used.

Example 6

Adhesive patches containing the composition (weight %) shown in Table 5 were prepared. In vitro transdermal permeability test with use of pig skin was conducted for the obtained patches. The results are shown in Table 5.

TABLE 5

|  | Ex. 6-1 M304 | Ex. 6-2 M306 | Ex. 6-3 M305 | Ex. 6-4 M307 | Com. 6-1 M291 | Com. 6-2 M295 | Com. 6-3 M300 | Com. 6-4 M303 |
|---|---|---|---|---|---|---|---|---|
| Oxyco. HCl 3H$_2$O | 3.461 | 3.461 | 3.461 | 3.461 | 3.461 | 3.461 | 3.461 | 3.461 |
| Sorbic Acid | 0.7 | 0.7 | | | | | | |
| Potassium sorbate | 1.3 | 1.3 | 1.3 | 1.3 | | | | |
| Diisopropanolamine | 1.5 | 1.5 | 1.5 | 1.5 | 1.5 | | 1.5 | 1.5 |
| Triethanolamine | | | | | | 2.1 | | |
| Potassium hydroxide | | | | | 0.55 | 0.56 | 0.55 | 0.55 |
| Levulinic acid | | | | 0.8 | 1.0 | 1.0 | 1.0 | 1.5 |
| Oleic acid | 3.0 | 3.0 | 3.0 | 3.0 | 4.0 | 4.0 | 4.0 | 4.0 |
| Myristic acid | | 5.0 | | | | | | |
| Oleyl alcohol | 10.0 | 10.0 | 10.0 | 10.0 | 3.0 | 10.0 | 10.0 | 10.0 |
| PEG200 | | | | | 5.0 | | | |
| Propylene carbonate | 5.0 | 5.0 | 5.0 | 5.0 | 3.0 | 4.0 | 5.0 | 5.0 |
| Glycerin | 5.00 | 5.00 | 5.00 | 5.00 | 5.00 | | | 5.00 |
| Medium-chain triglyceride | 10.0 | | 10.0 | 10.0 | 10.0 | 10.0 | 10.0 | 100 |
| Diethyl sebacate | | 5.0 | | | | | | |
| Liquid paraffin | 16.91 | 16.91 | 17.61 | 16.81 | 18.34 | 17.73 | 17.34 | 16.84 |
| AEROSIL ® | 3.0 | 3.0 | 3.0 | 3.0 | 3.0 | 3.0 | 3.0 | 3.0 |
| PX-1150N | 26.0 | 26.0 | 26.0 | 26.0 | 27.0 | 26.0 | 26.0 | 26.0 |
| SIS5002 | 15.0 | 15.0 | 15.0 | 15.0 | 15.0 | 15.0 | 15.0 | 15.0 |
| Sodium pyrosulfite | 0.1 | 0.1 | 0.1 | 0.1 | 0.1 | 0.1 | 0.1 | 0.1 |
| Sodium sulfite | | | | | | | | |
| Propyl gallate | 0.05 | 0.05 | 0.05 | 0.05 | 0.05 | 0.05 | 0.05 | 0.05 |
| Total | 100 | 100 | 100 | 100 | 100 | 100 | 100 | 100 |

TABLE 5-continued

|  |  | Ex. 6-1 M304 | Ex. 6-2 M306 | Ex. 6-3 M305 | Ex. 6-4 M307 | Com. 6-1 M291 | Com. 6-2 M295 | Com. 6-3 M300 | Com. 6-4 M303 |
|---|---|---|---|---|---|---|---|---|---|
| (base)/(sorbate component) | | 1.38 | 1.38 | 2.38 | 2.38 | | | | |
| (Sorbic acid)/(oxycodone) | | 1.73 | 1.73 | 1.00 | 1.00 | 0.00 | 0.00 | 0.00 | 0.00 |
| (aliphatic acid)(base) | | 1.25 | 2.33 | 0.94 | 1.28 | 1.05 | 0.93 | 1.05 | 1.25 |
| Cumulative skin | 2 hr | 0.881 | 0.858 | 0.675 | | 1.000 | 1.561 | | 0.08 |
| permeation | 4 hr | 10.39 | 6.52 | 11.23 | 0.997 | 11.22 | 14.28 | 0.491 | 6.088 |
| amount | 6 hr | 33.39 | 22.43 | 41.75 | 15.8 | 27.51 | 33.3 | 1.789 | 20.36 |
| ($\mu g/cm^2$) | 8 hr | 68.12 | 45.37 | 73.08 | 33.5 | 47.66 | 62.07 | 4.059 | 39.98 |
|  | 24 hr | 348.5 | 316.5 | 318.2 | 224.4 | 183.5 | 186.8 | 40.22 | 182.1 |

All adhesive patches of Examples 6-1 to 6-4 containing sorbic acid exhibit excellent skin permeability.

INDUSTRIAL APPLICABILITY

The percutaneous absorption composition of the present disclosure can be used as adhesive patches containing basic medicament such as tizanidine or oxycodone.

What is claimed is:

1. A percutaneous absorption non-aqueous composition comprising:
   tizanidine or a salt thereof; and
   sorbic acid,
   wherein a molar ratio of the sorbic acid to the tizanidine or the salt thereof is 0.5-3.0.
2. The percutaneous absorption composition according to claim 1, wherein the molar ratio of the sorbic acid to the tizanidine or the salt thereof is 0.9-2.5.
3. The percutaneous absorption composition according to claim 1, further comprising a basic component.
4. The percutaneous absorption composition according to claim 3, wherein a molar ratio of the basic component to the sorbic acid is 0.4-3.0.
5. The percutaneous absorption composition according to claim 3, wherein the basic component comprises one or more of an organic basic compound, an inorganic basic compound, and a salt of a strong base.
6. The percutaneous absorption composition according to claim 5, wherein the organic basic compound is a C2-9 alkanolamine.
7. The percutaneous absorption composition according to claim 6, wherein the C2-9 alkanolamine includes at least one selected from the group consisting of monoethanolamine, monoisopropanolamine, diethanolamine, diisopropanolamine, triethanolamine, triisopropanolamine, ethylenediamine, and trishydroxymethylaminomethane.
8. The percutaneous absorption composition according to claim 5, wherein the inorganic basic compound is a compound containing an alkali metal or an alkali earth metal.
9. The percutaneous absorption composition according to claim 5, wherein the organic basic compound is a basic amino acid.
10. The percutaneous absorption composition according to claim 5, wherein the salt of the strong base includes at least one of a metal salt of a carboxylic acid, a metal salt of a hydroxyl acid, and sodium pyrosulfite.
11. The percutaneous absorption composition according to claim 1, further comprising an ester compound.
12. The percutaneous absorption composition according to claim 11, wherein the ester compound includes at least one selected from the group consisting of diethyl sebacate, methyl laurate, diisopropyl adipate, isopropyl myristate, and medium-chain triglyceride.
13. The percutaneous absorption composition according to claim 1, further comprising an alcohol.
14. The percutaneous absorption composition according to claim 13, wherein the alcohol includes at least one selected from the group consisting of a monovalent alcohol, a divalent alcohol, and a trivalent alcohol.
15. The percutaneous absorption composition according to claim 1, further comprising an aliphatic acid other than the sorbic acid.
16. The percutaneous absorption composition according to claim 1, wherein the molar ratio of the sorbic acid to the tizanidine or a salt thereof is 2.1-3.0.
17. The percutaneous absorption composition according to claim 1, consisting of:
   the tizanidine or the salt thereof;
   the sorbic acid; and
   optionally at least one selected from the group consisting of an aliphatic acid other than the sorbic acid, a basic component, an ester compound, and an alcohol.
18. The percutaneous absorption composition according to claim 1, comprising the salt of tizanidine.
19. The percutaneous absorption composition according to claim 18, wherein the salt of tizanidine includes at least one selected from the group consisting of a hydrochloride salt, a sulfate salt, a hydrobromate salt, a fumarate, a maleate, a citrate, and a tartrate.
20. The percutaneous absorption composition according to claim 19, wherein the salt of tizanidine includes a hydrochloride salt.

* * * * *